(12) United States Patent
Hesse et al.

(10) Patent No.: US 6,608,239 B1
(45) Date of Patent: Aug. 19, 2003

(54) MEANS AND METHODS FOR ENHANCING THE CONTENT OF SULFUR COMPOUNDS IN PLANTS

(75) Inventors: Holger Hesse, Berlin (DE); Karsten Harms, Potsdam (DE); Rainer Hofgen, Golm (DE)

(73) Assignee: Max-Planck-Gesellschaft zur Forderung der Wissenschaften e.V., Berlin (DE)

( * ) Notice: Subject to any disclaimer, the term of this patent is extended or adjusted under 35 U.S.C. 154(b) by 0 days.

(21) Appl. No.: 09/743,254

(22) PCT Filed: Jul. 7, 1999

(86) PCT No.: PCT/EP99/04784
§ 371 (c)(1),
(2), (4) Date: Mar. 30, 2001

(87) PCT Pub. No.: WO00/01833
PCT Pub. Date: Jan. 13, 2000

(30) Foreign Application Priority Data

Jul. 7, 1998 (EP) .............................. 98112553

(51) Int. Cl.[7] .............................. A01H 1/00; A01H 9/00; C12N 15/82; C12N 15/87; C12N 15/00; C12N 15/09; C12N 15/63; C12N 15/70; C12N 15/74; C12N 9/10; C07H 21/04; C12P 13/12

(52) U.S. Cl. ..................... 800/278; 800/287; 800/288; 800/295; 536/23.2; 536/23.6; 435/113; 435/193; 435/320.1

(58) Field of Search .................. 800/278, 287, 800/288, 295; 536/23.1, 23.6; 435/320.1, 113, 193

(56) References Cited

U.S. PATENT DOCUMENTS 5,360,742 A * 11/1994 Rogers ..................... 435/320.1

FOREIGN PATENT DOCUMENTS

WO    WO 00/36127 A1    6/2000
WO    WO 00/55303 A2    9/2000

OTHER PUBLICATIONS

Saito, K. et al., Modulation of Cysteine Biosynthesis in Chloroplasts of Transgenic Tobacco Overexpressing Cysteine Synthase [O–Acetylserine(thiol)–lyase], Plant. Physiol., vol. 106, pp. 887–895 (1994).*

Youssefian et al., "Increased Cysteine Biosynthesis Capacity of Transgenic Tobacco Overexpressin an O–Acetylserine (thiol) Lyase Modifies Plant Responses to Oxidative Stress", Plant Physiol. vol. 126, 2001; pp. 1001–1011.

Dominguez–Solis et al., "The Cytosolic O–Acetylserine (thiol) lyase Gene Is Regulated by Heavy Metals and Can Function in Cadmium Tolerance", The Journal of Biological Chemistry vol. 276, No. 12, Issue of Mar. 23, pp. 9297–9302, 2001.

Blaszczyk et al., "Increased resistance to oxidative stress in transgenic tobacco plants overexpressing bacterial serine acetyltransferase", Blackwell Science Ltd, The Plant Journal, (1999), 20, 237–243.

* cited by examiner

Primary Examiner—Kenneth R. Horlick
Assistant Examiner—Teresa E Strzelecka
(74) Attorney, Agent, or Firm—Birch, Stewart, Kolasch & Birch, LLP

(57) ABSTRACT

Described are recombinant DNA molecules comprising a nucleic acid molecule encoding a protein having serine acetyltransferase (SAT) activity and optionally a nucleic acid molecule encoding a protein having cysteine-γ-synthase (CγS) activity; wherein said nucleic acid molecule(s) are operably linked to regulatory elements allowing the expression of the nucleic acid molecule(s) in plant cells. Also provided are vectors comprising said recombinant DNA molecules as well as plant cells, plant tissues and plants transformed therewith. In addition, the use of the aforementioned recombinant DNA molecules and vectors in plant cell and tissue culture, plant breeding and/or agriculture is described as well as the use of the aforementioned plants, plant tissue and plant cells for the production of food, feed and additives therefor.

20 Claims, 6 Drawing Sheets

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: EcSAT-N: Synthetic oligonucleotide used to
      amplify SAT from E. coli genomic DNA

<400> SEQUENCE: 1
gagagaccat ggcgtgtgaa gaactggaaa                              30

<210> SEQ ID NO 2
<211> LENGTH: 30
<212> TYPE: DNA
<213> ORGANISM: Artificial Sequence
<220> FEATURE:
<223> OTHER INFORMATION: EcSAT-C: Synthetic oligonucleotide used to
      amplify SAT from E. coli genomic DNA

<400> SEQUENCE: 2
gagagatcta gattagatcc catccccata                              30

MEANS AND METHODS FOR ENHANCING THE CONTENT OF SULFUR COMPOUNDS IN PLANTS

Figure 1A:

This application is the national phase under 35 U.S.C. § 371 of PCT International Application No. PCT/EP99/04784 which has an International filing date of Jul. 7, 1999, which designated the United States of America.

The present invention relates to a recombinant DNA molecule comprising a nucleic acid molecule encoding a protein having serine acetyltransferase (SAT) activity and optionally a nucleic acid molecule encoding a protein having cysteine-γ-synthase (CγS) activity; wherein said nucleic acid molecule(s) are operably linked to regulatory elements allowing the expression of the nucleic acid molecule(s) in plant cells. The present invention also provides vectors comprising said recombinant DNA molecules as well as plant cells, plant tissues and plants transformed therewith. The present invention further relates to the use of the aforementioned recombinant DNA molecules and vectors in plant cell and tissue culture, plant breeding and/or agriculture. Furthermore, the present invention involves the production of food, feed and additives therefor comprising the above-described plant cells, plant tissue and plants.

Higher plants use inorganic sulfate in the soil as the major sulfur source for synthesizing the sulfur-containing amino acids cysteine and methionine. Cysteine biosynthesis in plants has been postulated to play an essential role in the sulfur cycle in nature. Reduced sulfur in the form of cysteine is needed for many different functions in plants (Rennenberg, 1990; Schmidt, 1992). It is essential for the normal plant metabolism because of connecting serine and methionine metabolism by carrying the reduced sulfur necessary for methionine biosynthesis (Giovanelli, 1990; Ravanel, 1997; Brunold and Rennenberg, 1997). Additionally, cysteine serves as substrate for other sulfur containing molecules like certain co-factors, membrane compounds, and as an essential amino acid for protein synthesis (Giovanelli, 1980; Schmidt, 1992). Cysteine is also essential as a precursor for the production of glutathione (GSH) and other stress related metabolites. The demand for cysteine varies during plant development and is also dependend on changes in the environment, including light, sulfate availability and some kinds of stress, abiotic or biotic (von Arb and Brunold 1986; Nussbaum, 1988; Delhaize, 1989; Rauser, 1991; Ghisi, 1993; Hell, 1994).

For cysteine biosynthesis, first L-serine has to be activated by transfer of an acetyl-group from acetyl coenzyme A to form the intermediate O-acetyl-L-serine (OAS). This important reaction is catalized by serine acetyltransferase (SAT). The activation of serine, a key reaction in the cysteine biosynthetic pathway, has been investigated at the molecular level only in prokaryotes (Breton, 1990; Monroe, 1990; Evans, 1991; Lai and Baumann, 1992). The synthesis of cysteine in plants is accomplished by the sulfhydrylation of O-acetyl-L-serine in the presence of free or bound sulfide, catalyzed by O-acetylserine(thiol)-lyase (OAS-TL, cysteine synthase, CSase; E C 4.2.99.8.) (Schmidt and Jäger, 1990). This reaction has been extensively analysed (Saito, 1992, 1993 and 1994; Rolland, 1993 and 1996; Youssefian, 1993; Noji, 1994; Hell, 1994; Kuske, 1994 and 1996; Takahashi and Saito, 1996). In bacteria SAT and OAS-TL form a bifunctional complex called cysteine synthase. In this complex only a small proportion of the O-acetylserine(thiol) lyase (5%) is associated with all the SAT activity (Kredich, 1969). In addition, studies on the regulation of cysteine biosynthesis in bacteria revealed that serine acetyltransferase is sensitive to feedback inhibition by L-cysteine, and that O-acetylserine (or N-acetylserine) is involved in the transcriptional activation of several of the cys operon promotors (Ostrowski and Kredich, 1989; Kredich, 1993).

Plant cDNAs encoding serine acetyltransferases have recently been cloned from different species (Bogdanova, 1995; Murillo, 1995; Ruffet, 1995; Saito, 1995; Roberts and Wray, 1996). In plants, SAT also exists in a complex with OAS-TL, suggesting an efficient metabolic channeling from serine to cysteine by preventing the diffusion of the intermediate O-acetyl-L-serine (Nakamura, 1988; Nakamura and Tamura, 1990; Ruffet, 1994; Bogdanova and Hell, 1997; Hesse, 1997). Both SAT and OAS-TL have been reported to be localised in plastids, mitochondria and cytosol from several plants, suggesting that the ability to synthesize cysteine appears to be necessary in all cellular compartments with an endogenous protein biosynthetic capacity (Smith and Thompson, 1969; Smith, 1972; Brunold and Suter, 1982; Lunn, 1990; Rolland, 1992; Ruffet, 1994). In Pisum sativum for example, three different isoforms of SAT are existing, and each isoform seems to be specific for a given intracellular compartment (Ruffet, 1995). Beside these required cellular locations, the fact that cysteine biosynthesis is in complex interaction with uptake and reduction of sulfate, which itself is regulated by photosynthesis and nitrate assimilation (Anderson, 1990; Brunold, 1993), let suggest an important role of cysteine biosynthesis in sulfur metabolism in higher plants.

A very important feature of the reaction sequences of cysteine formation is the fact that SAT activity is much lower as compared to the activity of OAS-TL. In seeds and seedlings, OAS-TL is 10 to 20 times more active than SAT (Smith, 1971; Ngo and Shargool, 1974). In whole leaves the activity ratio of both enzymes is 100 to 300-fold (Nakamura, 1987), whereas in chloroplasts alone the ratio is up to 345-fold (Ruffet, 1994). As has been shown in Allium and spinach, SAT is in comparison to OAS-TL a low abundance enzyme (Nakamura and Tamura, 1990; Ruffet, 1994). Additionally, the availability of OAS was also discussed to be rate limiting for cysteine synthesis (Neuenschwander, 1991; Ghisi, 1990; Rennenberg 1983; Brunold, 1993; Saito, 1994). SAT activity is significantly regulated by feedback inhibition of cysteine in watermelon (Saito, 1995). Also on gene expression level SAT regulation takes place. In *Arabidopsis thaliana* in response to light and sulfur stress SAT mRNA accumulates by about twofold (Bogdanova, 1995). However, while the function and role of SAT, OAS and OAS-TL in the reaction cascade of cysteine biosynthesis have been subject to a lot of investigations previous attempts to alter the rate of cysteine synthesis failed (Saito, 1994). Hence, the precise regulation of the cysteine biosynthetic pathway is still not fully understood and part of controversial discussion. Therefore, means for the control the sulfur content in plants that may have applications in several aspects of agriculture were hitherto not available.

Thus, the technical problem underlying the present invention was to comply with the need for means and methods for modulating the content of sulfur compounds in plants.

The solution to this technical problem is achieved by providing the embodiments characterized in the claims.

Accordingly, the invention relates to a recombinant DNA molecule comprising (a) a nucleic acid molecule encoding a protein having serine acetyltransferase (SAT) activity, and optionally (b) a nucleic acid molecule encoding a protein having cysteine-γ-synthase (CγS) activity;

wherein said nucleic acid molecule(s) are operably linked to regulatory elements allowing the expression of the nucleic acid molecule(s) in plant cells.

The term "protein having serine acetyltransferase (SAT) activity", as used herein, means that said protein is able to transfer an acetyl-group from acetyl coenzyme A to L-serine to form the intermediate of the cysteine biosynthetic pathway O-acetyl-L-serine.

The term "protein having cysteine-γ-synthase (CγS) activity" in accordance with the present invention denotes a protein capable of catalyzing the formation of L-cystathionine or L-homocysteine depending on the sulfur-containing substrate, L-cysteine or sulfide. This protein is also known as cystathionine γ-synthase. The terms "cysteine-γ-synthase" and "cystathionine γ-synthase" are used interchangeable herein. In plants CγS usually catalyses the first reaction specific for methionine biosynthesis, namely the gamma-replacement of the phosphoryl substituent of O-phosphohomoserine by cysteine. Thus, cysteine is a major precursor in the biosynthesis of methionine in plants.

In accordance with the present invention, the coding sequence of the cysE gene from *Escherichia coli* (Denk and Böck, 1987), which encodes an enzyme of the cysteine biosynthetic pathway, namely serine acetyltransferase (SAT, EC 2.3.1.30), was introduced into the genome of potato plants under the control of the cauliflower mosaic virus (CaMV) 35S promoter. To target the protein into the chloroplast cysE was translationally fused to the 5'-signal sequence of the small subunit of rubisco; see Example 1. Successfully transformed plants showed a high accumulation of the cysE mRNA. Furthermore, crude leaf extracts of these plants had a significant high SAT-activity, being up to 20 fold higher as compared to wild type plants. The transgenic potato plants overexpressing the *E. coli* gene exhibited elevated levels of cysteine and glutathione (GSH), being two to threefold higher than in control plants; see Example 2. However, surprisingly the elevation of SAT enzyme activity and of the substrate for cysteine biosynthesis O-acetyl-L-serine (OAS) had no effect on the expression and on the activity of O-acetylserine(thiol)-lyase (OAS-TL), the enzyme which converts OAS, the product of SAT, to cysteine; see Examples 3 and 4. Both the expression of this gene on RNA level and the enzyme activity remained unchanged compared to wild type plants.

From these experiments, the following conclusions were reached: on one hand the bacterial *E. coli* SAT expressed in the transgenic potato plants was accumulated as a catalytically functional protein in the chloroplasts. On the other hand the cellular contents of cysteine and glutathione were significantly increased in leaves of the transgenic plants. The levels of cysteine in one transformant (SAT-48) were nearly threefold and in another transformant (SAT-26) twofold higher than those amounts found in nontransformed control plants, indicating that the expression of cysE is responsible for the stimulation of cysteine synthesis. The experiments performed in accordance with the present invention also revealed that both transformants had significantly elevated glutathione levels, being up to twofold higher than in wild type plants. These unexpected results demonstrate that under normal conditions without any sulfur stress, the endogenous level of SAT is a limiting step in the cysteine biosynthetic pathway, at least in the chloroplast, where the *E. coli* SAT was targeted to. This means that under usual conditions the level of OAS-TL is sufficient for converting all the OAS produced in the cell and thereby is not limiting for a normal flux of cysteine biosynthesis. The fact, that an overexpression of the SAT in the transgenic potato plants is able to increase the cysteine and glutathione content further implicates that the steps in the sulfate assimilation pathway before the incorporation of sulfide into cysteine, i.e. sulfate uptake, sulfate activation and reduction of adenosine 5'-phosphosulfate (APS), are under normal conditions also not limiting for cysteine biosynthesis. The plants seem to possess enough sulfate uptake capacity and activities to convert sulfate to sulfide for providing sufficient quantities of reduced sulfur, necessary for the production of cysteine. Finally it is worth mentioning, that the results presented in accordance with the present invention directly show the connection between free cysteine and glutathione. The increased levels of cysteine in the transgenic potato plants stimulate the biosynthesis of glutathione, leading to levels of the tripeptide, which are up to twofold higher as compared to wild type plants. This suggests, that glutathione biosynthesis in potato leaves is limited by the availability of cysteine. Recently performed experiments with poplar confirm these results (Strohm, 1995; Noctor, 1996).

As has been revealed in the experiments performed in accordance with the present invention, plants possess enough sulfate uptake capacity and activities to convert sulfate to sulfid for providing sufficient amounts of reduced sulfur, necessary for the biosynthesis of sulfur containing compounds. Thus, based on the findings of the present invention, it can be expected that by introducing cysteine-γ-synthase, the first enzyme specific for the methionine biosynthetic pathway in transgenic plants, the content of methionine could be significantly increased in plants compared to wild type. In this respect, it is noted that an increase of the content of sulfur containing compounds in plants of at least 10% already confer advantageous effects to the plant, for example enhanced tolerance to abiotic stress. Preferably the content of these compounds is increased by at least about 50%, most preferably 100% and particularly preferred is the increase of the content of sulfur containing compounds of more than 1, preferably 2-fold. Locke, Keystone Meeting Apr. 6–11, 1997, Abstract 306 (1997) reported the increase of methionine by 3 to 5 fold when expressing CγS in plants. Since the introduction of SAT results in an increase of the substrate of CγS it is expected by introducing the CγS in SAT expressing plants of the invention or vice versa the increase of the content of sulfur containing compounds is further increased about 1 to 10 fold, preferably 5 to 10 fold or higher.

In a preferred embodiment of the recombinant DNA molecule of the inventiori, said protein having SAT activity is a serine acetyltransferase derived from prokaryotes or archaebacteria. Prokaryotic organisms may include gram negative as well as gram positive bacteria such as, for example, *E. coli, S. typhimurium, Serratia marcescens, Bacillus subtilis* and various species within the genera Pseudomonas, Streptomyces and Staphylococcus, although others may also be employed as well. For example, nucleic acid molecules encoding proteins having SAT activity can be obtained from the prior art (e.g., Bogdanova, FEBS Lett. 358 (1995), 43–47; Denk, J. Gen. Microbiol. 133 (1987), 515–525; Evans, J. Bacteriol. 173 (1991), 5457–5469).

In general the nucleic acid molecule encoding a protein having CγS activity can be derived from any material source, for example, from any plant possessing such molecules, preferably form monocotyledonous or dicotyledonous plants, in particular from any plant of interest in agriculture, horticulture or wood culture, such as crop plants, namely those of the family Poaceae, any starch producing plants, such as potato, maniok, leguminous plants, oil producing plants, such as oilseed rape, linenseed, etc., plants using polypeptide as storage substances, such as soybean, plants using sucrose as storage substance, such as sugar beet or sugar cane, trees, ornamental plants etc. or plants belonging to the family Gramineae. Nucleic acid molecules encoding cysteine γ-synthase are described in the prior art, for example, in Ravanel, Biochem. J. 331 (1998), 639–648 and references cited therein.

Furthermore, nucleic acid molecules can be used hybridizing to the above-described nucleic acid molecules and encoding a protein having SAT and CγS activity, respectively. Such nucleic acid molecules can be isolated, e.g., from libraries, such as cDNA or genomic libraries by techniques well known in the art. For example, hybridizing nucleic acid molecules can be identified and isolated by using the above-described nucleic acid molecules known in the art or fragments thereof or complements thereof as probes to screen libraries by hybridizing with said molecules according to standard techniques. Possible is also the isolation of such nucleic acid molecules by applying the polymerase chain reaction (PCR) using as primers oligonucleotides derived form the above-described nucleic acid molecules. Nucleic acid molecules which hybridize with any of the aforementioned nucleic acid molecules also include fragments, derivatives and allelic variants of the above-described nucleic acid molecules that encode a protein having SAT or CγS activity or biologically active fragments thereof. Fragments are understood to be parts of nucleic acid molecules long enough to encode the described protein or a fragment thereof having the biological activity as defined above.

The term "derivative" means in this context that the nucleotide sequence of these nucleic acid molecules differs from the sequences of the above-described nucleic acid molecules in one or more nucleotide positions and are highly homologous to said nucleic acid molecules. Homology is understood to refer to a sequence identity of at least 40%, particularly an identity of at least 60%, preferably more than 80% and still more preferably more than 90%. The deviations from the sequences of the nucleic acid molecules described above can, for example, be the result of nucleotide substitution(s), deletion(s), addition(s), insertion(s) and/or recombination(s) either alone or in combination, that may naturally occur or be produced via recombinant DNA techniques well known in the art; see for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Homology further means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological activity as defined herein. They may be naturally occurring variations, such as SAT and CγS protein encoding sequences from other prokaryotes and plants, respectively, or mutations. These mutations may occur naturally or may be obtained by mutagenesis techniques, see supra. The allelic variations may be naturally occurring allelic variants as well as synthetically produced or genetically engineered variants; see supra. For example, the amino acid sequences of plant SATs share significant similarities with bacterial serine acetyltransferases (Vuorio, 1994; Bogdanova and Hell, 1997). The most conserved region within all SATs, both from plants and bacteria, is located at the C-terminus and has been suggested to confer the transferase activity (Vaara, 1992; Vuorio, 1994). In this conserved region a hexapeptide motif is present that has been proposed as a catalytic domain in bacterial acetyltransferases and that recently has been demonstrated to be also present in the OAS-TL/SAT contact region in the cysteine synthase complex from *Arabidopsis thaliana* (Bogdanova and Hell, 1997). In addition, nucleic acid molecules can be employed in accordance with the present invention that encode homologs or analogs of the above described proteins having SAT or CγS activity but where otherwise unrelated to those proteins. For example, malY of *E. coli* encodes an enzyme that is involved in the uptake and metabolism of maltose and maltodextrins of the *E. coli* maltose system but has in addition the enzyme activity of cystathionine β-lyase; see Zdych, J. Bacteriol. 177 (1995), 5035–5039. However, said proteins are not homologous to each other based on amino acid sequence homology analysis. Such proteins that do not display significant homologies to common SAT or CγS proteins can be identified by a person skilled in the art using techniques well known in the art, for example, via complementation of mutant genes involved in the cysteine or methionine biosynthetic pathway, for example, in corresponding mutant *E. coli* strains; see also Zdych, supra.

The proteins encoded by the various derivatives, variants, homologs or analogs of the above-described nucleic acid molecules may share specific common characteristics, such as molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc. All these nucleic acid molecules and derivatives can be employed in accordance with the present invention as long as the enzymatic activity of the encoded protein remains substantially unaffected in kind, namely that the protein has SAT and CγS activity, respectively, as defined above.

In a preferred embodiment of the recombinant DNA molecule of the invention, the protein having CγS-activity is cysteine-γ-synthase from potato, tabacco, tomato, rape seed or Arabidopsis; see, e.g., Kim and Leustek, Plant Mol. Biol. 32 (1996), 1117–1124.

In a preferred embodiment of the recombinant DNA molecule of the invention, the nucleic acid molecule of (a) and/or (b) is operably linked to a nucleotide sequence encoding a transit peptide capable of directing the protein(s) into a desired cellular compartment. The nucleic acid molecule present in the recombinant DNA molecule according to the invention can be modified in such a way that the encoded protein is located in any desired compartment of the plant cell. These include the endoplasmatic reticulum (KDEL, Schouten, Plant Mol. Biol. 30 (1996), 781–793), the vacuole (Neuhaus, PNAS 88 (1991), 10362–10366), the mitochondria (Chaumont, Plant Mol. Biol. 24 (1994), 631–641), the plastids (Fuhr, EMBO J. 5 (1986), 2063–2071), the apoplast (von Schaewen, EMBO J. 9 (1990), 3033–3044), the cytoplasm etc. Methods how to carry out these modifications and signal sequences ensuring localization in a desired compartment are well known to the person skilled in the art. Preferably, said cellular compartment is a plastid. As is described in the appended examples, the protein having SAT activity was targeted into the chloroplast via the translational fusion to the 5'-signal sequence of the small subunit of rubisco. Advantageously, the protein having CγS activity may be coexpressed in the same cellular compartment, for example in the chloroplast and should, therefore, provide for significant increase of methionine content in plant leafs as well.

The recombinant DNA molecule of the invention comprises regulatory sequences allowing for the expression the nucleic acid molecules in plant cells. Preferably, said regulatory elements comprise a promoter active in plant cells. Expression comprises transcription of the nucleic acid molecule into a translatable mRNA. Regulatory elements ensuring expression in plant cells are well known to those skilled in the art.

These regulatory elements may be heterologous or homologous with respect to the nucleic acid molecule to be expressed as well with respect to the plant species to be transformed. In general, such regulatory elements comprise a promoter active in plant cells. To obtain expression in all tissues of a transgenic plant, preferably constitutive promoters are used, such as the 35S promoter of CaMV (Odell, Nature 313 (1985), 810–812) or promoters of the polyubiquitin genes of maize (Christensen, Plant Mol. Biol. 18 (1982), 675–689). In order to achieve expression in specific tissues of a transgenic plant it is possible to use tissue specific promoters (see, e.g., Stockhaus, EMBO J. 8 (1989), 2245–2251). Known are also promoters which are specifically active in tubers of potatoes or in seeds of different plant species, such as maize, Vicia, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Test-system may be employed (Gatz, Mol. Gen. Genet. 227 (1991); 229–237). Further suitable promoters are known to the person skilled in the art and are described, e.g., in Ward (Plant Mol. Biol. 22 (1993), 361–366). The regulatory elements may further comprise transcriptional and/or translational enhancers functional in plants cells. A plant translational enhancer often used is, e.g., the CaMV omega sequences and/or the inclusion of an intron (Intron-1 from the Shrunken gene of maize, for example) that has been shown to increase expression levels by up to 100-fold. (Maiti, Transgenic Research 6 (1997), 143–156; Ni, Plant Journal 7 (1995), 661–676). Furthermore, the regulatory elements may include transcription termination signals, such as a poly-A signal, which lead to the addition of a poly A tail to the transcript which may improve its stability. The termination signals usually employed are from the Nopaline Synthase gene or from the CaMV 35S RNA gene.

In a preferred embodiment of the recombinant DNA molecule of the invention, said promoter is inducible or constitutively expressed and/or is a cell, tissue or organ specific promoter. Preferably, said promoter is tuber-specific, seed-specific, endosperm-specific, embryo-specific, or phloem-specific. Examples for such promoters include but are not limited to patatin promoter B33 (tuber-specific, Rocha-Sosa, EMBO J. 8 (1989), 23), phaseolin promoter (seed-specific, Karchi, Plant J. 3 (1993), 721–727), HMW glutenin promoter (endosperm-specific, Helford, Theor. Appl. Genet. 75 (1987), 117–126), α, β-conglycin promoter (embryo-specific, Fujiwara, Plant Cell Reports 9 (1991), 602–606), rolC promoter (phloem-specific, Lerchl, Plant Cell 7 (1995), 259–270).

The present invention also relates to vectors, particularly plasmids, cosmids, viruses, bacteriophages and other vectors used conventionally in genetic engineering that contain at least one recombinant DNA molecule according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the recombinant DNA molecules and vectors of the invention can be reconstituted into liposomes for delivery to target cells.

Advantageously the above-described vectors of the invention comprises a selectable and/or scorable marker. Selectable marker genes useful for the selection of transformed plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143–149); npt, which confers resistance to the aminoglycosides neomycin, kanamycin and paromycin (Herrera-Estrella, EMBO J. 2 (1983), 987–995) and hygro, which confers resistance to hygromycin (Marsh, Gene 32 (1984), 481–485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from Aspergillus terreus which confers resistance to Blasticidin S (Tamura, Biosci. Biotechnol. Biochem. 59 (1995), 2336–2338). Useful scorable marker are also known to those skilled in the art and are commercially available. Advantageously, said marker is a gene encoding luciferase (Giacomin, Pl. Sci. 116 (1996), 59–72; Scikantha, J. Bact. 178 (1996), 121), green fluorescent protein (Gerdes, FEBS Lett. 389 (1996), 44–47) or β-glucuronidase (Jefferson, EMBO J. 6 (1987), 3901–3907). This embodiment is particularly useful for simple and rapid screening of cells, tissues and organisms containing a vector of the invention.

The recombinant DNA molecules according to the invention are in particular useful for the genetic manipulation of plant cells, plant tissue and plants in order to enhance their content of sulfur containing compounds and to obtain plants with modified, preferably with improved or useful phenotypes. Thus, the present invention provides for a method for the production of transgenic plants, plant cells or plant tissue comprising the introduction of at least one recombinant DNA molecule or vector of the invention into the genome of said plants, plant cells or plant tissue.

Methods for the introduction of foreign DNA into plants are also well known in the art. These include, for example, the transformation of plant cells, plant tissue or plants with T-DNA using Agrobacterium tumefaciens or Agrobacterium rhizogenes, the fusion of protoplasts, direct gene transfer (see, e.g., EP-A 164 575), injection, electroporation, biolistic methods like particle bombardment and other methods known in the art. The vectors used in the method of the invention may contain further functional elements, for example "left border"- and "right border"-sequences of the T-DNA of Agrobacterium which allow for stably integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13 (1989), 151–161; Peng, Plant Mol. Biol. 27 (1995), 91–104) and/or by using systems which utilize enzymes capable of promoting homologous recombination in plants (see, e.g., WO97/08331; Bayley, Plant Mol. Biol. 18 (1992), 353–361); Lloyd, Mol. Gen. Genet. 242 (1994), 653–657; Maeser, Mol. Gen. Genet. 230 (1991), 170–176; Onouchi, Nucl. Acids Res. 19 (1991), 6373–6378). Methods for the preparation of appropriate vectors are described by, e.g., Sambrook (Molecular Cloding; A Laboratory Manual, 2nd Edition (1989), Cold Spring Harbor Laboratory Press, Cold Spring Harbor, N.Y.).

Suitable strains of Agrobacterium tumefaciens and vectors as well as transformation of Agrobacteria and appropriate growth and selection media are well known to those skilled in the art and are described in the prior art (GV3101 (pMK90RK), Koncz, Mol. Gen. Genet. 204 (1986), 383–396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467–8471; Koncz, Plant Mol. Biol. 20 (1992), 963–976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1–22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1–46; An, EMBO J. 4 (1985), 277–287). Although the use of Agrobacterium tumefaciens is preferred in the method of the invention, other Agrobacterium strains, such as Agrobacterium rhizogenes, may be used, for example if a phenotype conferred by said strain is desired.

Methods for the transformation using biolistic methods are well known to the person skilled in the art; see, e.g., Wan, Plant Physiol. 104 (1994), 37–48; Vasil, Bio/Technology 11 (1993), 1553–1558 and Christou (1996) Trends in Plant Science 1, 423–431. Microinjection can be performed as described in Potrykus and Spangenberg (eds.), Gene Transfer To Plants. Springer Verlag, Berlin, N.Y. (1995). The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc.

In general, the plants, plant cells and plant tissue which can be modified with a recombinant DNA molecule or vector according to the invention and which show (over) expression of a proteins having SAT and optionally CγS activity, respectively, can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, peanut, soybean, etc.), cotton, sugar beet, sugar cane, leguminous plants (e.g. beans, peas etc.), wood producing plants, preferably trees, etc.

Thus, the present invention relates also to transgenic plant cells which contain stably integrated into the genome a nucleic acid molecule according to the invention linked to regulatory elements which allow for expression of the nucleic acid molecule in plant cells and wherein the nucleic acid molecule is foreign to the transgenic plant cell. By "foreign" it is meant that the nucleic acid molecule is either heterologous with respect to the plant cell, this means derived from a cell or organism with a different genomic background, or is homologous with respect to the plant cell but located in a different genomic environment than the naturally occurring counterpart of said nucleic acid molecule. This means that, if the nucleic acid molecule is homologous with respect to the plant cell, it is not located in its natural location in the genome of said plant cell, in particular it is surrounded by different genes. In this case the nucleic acid molecule may be either under the control of its own promoter or under the control of a heterologous promoter. The vector or recombinant DNA molecule according to the invention which is present in the host cell may either be integrated into the genome of the host cell or it may be maintained in some form extrachromosomally.

Alternatively, a plant cell having (a) nucleic acid molecule(s) encoding a protein having SAT and optionally CγS activity present in its genome can be used and modified such that said plant cell expresses the endogenous gene(s) corresponding to these nucleic acid molecules under the control of an heterologous promoter and/or enhancer elements. The introduction of the heterologous promoter and mentioned elements which do not naturally control the expression of a nucleic acid molecule encoding either of the above described proteins using, e.g., gene targeting vectors can be done according to standard methods, see supra and, e.g., Hayashi, Science 258 (1992), 1350–1353; Fritze and Walden, Gene activation by T-DNA tagging. In *Methods in Molecular* biology 44 (Gartland, K. M. A. and Davey, M. R., eds). Totowa: Human Press (1995), 281–294) or transposon tagging (Chandlee, Physiologia Plantarum 78 (1990), 105–115). Suitable promoters and other regulatory elements such as enhancers include those mentioned hereinbefore.

The presence and expression of the nucleic acid molecule(s) present in the recombinant DNA molecule or vector in the transgenic plant cells lead(s) to the synthesis of proteins which has (have) an influence on, e.g., stress resistance of the plant cells and leads to corresponding physiological and phenotypic changes in plants containing such cells. As is described in the appended examples, plants constitutively expressing *E. coli* SAT display high levels of cysteine. Additionally, the content of the tripeptide glutathione (γ-glutamylcysteineylglycine) was considerably higher than in wild type plants, because this compound is the main storage form of reduced sulfur in plant kingdom and serves as the major sink of produced cysteine. Glutathione plays not only an essential role in the regulation of sulfur nutrition, but is also an important factor in the defense of plants against various forms of stress, including high light intensities, drought, cold, heat and mineral deficiency (Smith, 1990; Rennenberg and Brunold, 1994). The tripeptide is synthesized in plants as well as in other organisms in two enzyme-catalyzed reactions from the constituent amino acids (Meister and Anderson, 1983; Rennenberg, 1995).

As discussed above, cysteine-γ-synthase is capable of using cysteine as the sulfur-containing substrate. Therefore, since it has been demonstrated in the course of the present invention, that transgenic plants overexpressing a protein having SAT activity have a considerably higher content of cysteine, coexpression of a nucleic acid molecule encoding a protein having CγS activity should provide for a synergistic effect in the production of methionine, since both the key-enzyme of the methionine biosynthetic pathway and its substrate are overproduced in the plants. Therefore, in a preferred embodiment of the invention, said plant cell comprises (a) recombinant DNA molecule(s) comprising (a) a nucleic acid molecule encoding a protein having serine acetyl transferase (SAT) activity, and (b) a nucleic acid molecule encoding a protein having cysteine-γ-synthase (CγS) activity;

wherein said nucleic acid molecule(s) are operably linked to regulatory elements as described above.

As is immediately evident to the person skilled in the art, the recombinant DNA molecule of the present invention can carry the nucleic acid molecules as defined in (a) and (b) either alone or in combination. The same applies to the above described vectors of the present invention as Well as to plant cells, plant tissue and plants transformed therewith. Likewise, said nucleic acid molecules may be under the control of the same regulatory elements or may be separately controlled for expression. In this respect, the person skilled in the art will readily appreciate that the nucleic acid molecules encoding a protein having SAT and CγS activity, respectively, can be expressed in the form of a single mRNA as transcriptional and optionally translational fusions. This means that the proteins having SAT and CγS activity, respectively, are produced as separate polypeptides or in the latter option as a fusion polypeptide that is further processed into the individual proteins, for example via a cleavage site for proteinases that has been incorporated between the amino acid sequences of both proteins. Of course, the proteins having SAT and CγS activity, respectively, may also be expressed as a bi- or multifunctional polypeptide, preferably disposed by a peptide linker which advantageously allows for sufficient flexibility of both proteins. Preferably said peptide linker comprises plural, hydrophilic, peptide-bonded amino acids of a length sufficient to span the distance between the C-terminal end of one of said proteins and the N-terminal end of the other of said proteins when said polypeptide assumes a conformation suitable for biological activity of both proteins when disposed in aqueous solution in the plant cell. Furthermore, the recombinant DNA molecules and vectors of the invention may comprise further genes encoding other proteins involved in cysteine and/or methionine biosynthesis. Examples for the above-described expression strategies can be found in the literature, e.g., for dicistronic mRNA (Reinitiation) in Hefferon, J. Gen. tirol. 78 (1997), 3051–3059, fusion proteins are described in Brinck-Peterson, Plant Mol. Biol. 32 (1996), 611–620 and Hotze, FEBS Lett. 374 (1995), 345–350; bifunctional proteins are discussed in Lamp, Biochem. Biophys. Res. Com. 244 (1998), 110–114 and Dumas, FEBS Lett. 408 (1997), 156–160 and for linker peptide and protease it is referred to Doskeland, Biochem. J. 313 (1996), 409–414.

In a preferred embodiment of the invention, the transgenic plant cell comprises a selectable marker. As described above, various selectable markers can be employed in accordance with the present invention. Advantageously, selectable markers may be used that are suitable for direct selection of transformed plants, for example, the phophinothricin-N-acetyltransferase gene the gene product of which detoxifies the herbicide L-phosphinothricin (glufosinate or BASTA); see, e.g., De Block, EMBO J. 6 (1987), 2513–2518 and Drnge, Planta 187 (1992), 142–151.

Furthermore, the present invention also relates to transgenic plants and plant tissue comprising the above-described transgenic plant cells or obtainable by the above described method. These may show, for example, improved stress resistance. Preferably, the level of glutathione, cysteine and/or methionine in the transgenic plant of the invention is increased compared to a wild type plant. An increase of the level of glutathione, cysteine and/or methionine is understood to refer to an elevated content of any one of the above cited sulfur containing compounds either alone or in combination in the transgenic plant cells, plant tissue or plants of the present invention in the order of at least about 10% compared to the corresponding non-transformed wild type plant cell, plant tissue or plant, which already provides for beneficial effects on the vitality of the plant such as, e.g., improved stress tolerance. Advantageously, the content of the above-described compounds is increased by at least about 50%, preferably by more than about 75%, particularly preferred at least about or more than 100% and still more preferably more than about 200%. Considering the content of cysteine, methionine and glutathione in combination even an 10- to 20-fold increase of sulfur containing compounds compared to the level of free cysteine in wild type plants can be achieved although higher increases of sulfur containing compounds in the plants of the present invention are envisaged as well.

Advantageously, the level of free cysteine in the plants of the present invention is about higher than 20 nmol per gram fresh weight (gfw) of leaf tissue, preferably higher than 30 nmol/gfw and more preferably higher than 40 nmol/gfw, see also Example 2. Furthermore, the content of glutathione in the plants of the present invention can be preferably higher than 350 nmol/gfw, more preferably higher than 500 nmol/gfw. The content of methionine can be increased by at least about 5 fold, preferably more than 10 fold.

In yet another aspect, the invention also relates to harvestable parts and to propagation material of the transgenic plants according to the invention which contain transgenic plant cells described above, i.e. at least one recombinant DNA molecule or vector according to the invention and/or which are derived from the above described plants and display increased levels of sulfur containing compounds as described supra. Harvestable parts can be in principle any useful parts of a plant, for example, leaves, stems, fruit, seeds, roots etc. Propagation material includes, for example, seeds, fruits, cuttings, seedlings, tubers, rootstocks etc.

Furthermore, the present invention relates to use of at least one recombinant DNA molecule or vector of the invention for the production of transgenic plants which display an increased level of glutathione, cysteine and/or methionine. Preferably, said increased level of methionine or cysteine results in accelerated maturation processes, altered flowers and/or pathogen resistance.

The constitutive expression of the *E. coli* SAT cysE gene in transgenic potato plants directly demonstrate in vivo, that the SAT-catalyzed reaction is indeed rate-limiting in the plant cysteine biosynthetic pathway, as is shown by the high levels of cysteine in the transformants; see the appended examples. Furthermore, as discussed above, it is expected that the corresponding high levels of glutathione in the transgenic plants are able to confer resistance against various forms of stress. In plants glutathione plays an important role in the defense against active oxygen species, xenobiotics, heavy metals and other forms of stresses including drought, heat and mineral deficiency (Alscher, 1989; Smith, 1990; Schmidt and Jäger, 1992; Rennenberg and Brunold, 1994; Rennenberg, 1995). Knowledge about this is also of practical importance. Higher resistance of plants against active oxygen species may play a very important role in future, thinking of the elevated ozon concentrations in the atmosphere. Furthermore, an increased tolerance against xenobiotics, for example herbicides, as a result of higher glutathione levels in the plants of the invention is reasonable. Moreover, a possible strategy is to construct transgenic plants which are able to grow on higher concentrations of heavy metal ions and which therefore could be used for bioremidation. Furthermore, the recombinant DNA molecules and vectors according to the invention may be useful for the alteration or modification of plant/pathogen interaction. The term "pathogen" includes, for example, bacteria, viruses and fungi as well as protozoa.

As discussed above, the transgenic plant cells, tissue and plants of the invention can be used to ameliorate the toxic effects of pollutants in soil including the water economy. Pollutants may be naturally present or be caused by mining, manufacturing and urban activities. Such pollutants comprise compounds which may inactivate sulfur containing proteins, in particular enzymes or act as antagonists or inhibitors in the cysteine and/or methionine biosynthetic pathway. Examples for such antagonists or inhibitors are herbicides, fungicides, pesticides or particularly metal ions, e.g., $Hg^{2+}$. For example, due to the elevated levels of GSH conferred by the expression of the nucleic acid molecules contained in the recombinant DNA molecules and vectors of the present invention in the above described plants it is possible to employ soil for agriculture which is otherwise not suitable because of the presence of, for example, toxic compounds which interfere with the sulfur containing enzymes and thus with plant growth. This is in particular true for soil which contains large amounts of heavy metals. Moreover, the plant cells, plant tissue and plants of the present invention can be used for remediation of soil contaminated with pollutants. An advantageous side effect is that by, for example, increased metal tolerance due to the presence of the recombinant DNA molecule or vector of the invention, the plant cells, plant tissue and plant of the present invention can be used for "biomining" (Cunningham, TIBTECH 13 (1995), 393–397). This means that the plants, plant tissue and plant cells of the present invention can be used for phytoextraction of metals such as mercury, nickel and copper. Furthermore, as mentioned before a higher content of GSH in the plant cells, plant tissue and plants of the invention can provide for increased resistance. In addition, the high level of GSH present in the above-described plant cells or plant tissues and plants is expected to result in improved growth of seedlings and biomass production. In summary, increase of the GSH content has manyfold effects on the vitality of plants and is of particular interest for the plant breeder.

Furthermore, overexpression of cysteine-γ-synthase in plants in combination with the SAT encoding nucleic acid molecule in transgenic plant cells, plant tissue and plants of the invention results in an increase of free as well as bound methionine in the plants, which is particularly advantageous for food and feed, since methionine is an essential amino acid and usually present only in low amounts in food and feed stuffs that, therefore, are not sufficient for the supply of this amino acid to humans and animals. Thus, the plant cells, plant tissues and plants as well as the harvestable parts and/or propagation material thereof can be used as feed or food or as additives therefor. Furthermore, the increase of methionine can enhance maturation processes, flowering as well as pathogen resistance. Also, high methionine contents in plants or harvestable parts thereof as well as propagation material of the invention significantly contribute to the attractive taste of various food products such as baked bread and roast coffee and the like.

Thus, the present invention relates in a further embodiment to use of a nucleic acid molecule encoding a protein having SAT activity or at least one recombinant DNA molecule or vector of the invention, a plant cell, a plant or plant tissue of the invention or, harvestable parts or propagation material thereof for the production of food, animal feed, for the improvement of pathogen resistance, for conferring heavy metall or herbicide tolerance, for improving biomass production, for enhancing growth of seedlings, for conferring tolerance against biotic or abiotic stress, or for improving the flavour and/or taste of food or feed. The use of the recombinant DNA molecule or vector of the invention for conferring herbicide tolerance includes, for example, their use as selectable markers in plants according to other systems which employ (over)expression of enzymes capable of conferring tolerance (i.e. resistance) to plant cell killing effects of herbicides. An example for such a system is the overexpression of the enzyme 5-enolpyruvylshikimate-3-phosphate (EPSP) synthase that confers tolerance to the herbicide glyphosphate. In a similar way, the recombinant DNA molecules and vectors of the invention can be used for conferring tolerance against compounds that act on sulfur containing enzymes via, e.g., sequestering the compound that is responsible for inhibition of said enzymes by the high content of cysteine, GSH and/or methionine or by peptides and proteins that are present in higher levels due to the elevated content of the sulfur containing amino acids.

As described above, the nutrional value of the plants, plant tissue and plant cells of the invention as well as harvestable parts and propagation material of such plants is considerably improved due to the increased content of sulfur containing compounds. Therefore, the present invention also relates to feed and food or additives therefor comprising plant cells, plant tissue, plant, harvestable parts or propagation material of the invention. These feed, food and additives preferably have increased contents of cysteine, methionine and/or glutathione such as described above.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352–364.

THE FIGURES SHOW

FIG. 1: (a) Northern blot analysis of total RNA extracted from leaves of five independent trangenic (SAT-65, 26, 48, 3 and 71) and two wild type plants (Control a and b). The blot was probed with $^{32}$P-labeled cysE DNA from *E. coli*. The lanes contained 15 μg of total RNA each.

(b) Maximum catalytic activity of SAT in leaves of five independent transgenic (SAT-65, 26, 48, 3 and 71) and two wild type plants (Control a and b). The specific activity of crude extracts is given in pmol produced CoA per min and μg total protein. Error bars represent standard deviation (<10%). N=4 independent measurements.

Figure 2A:
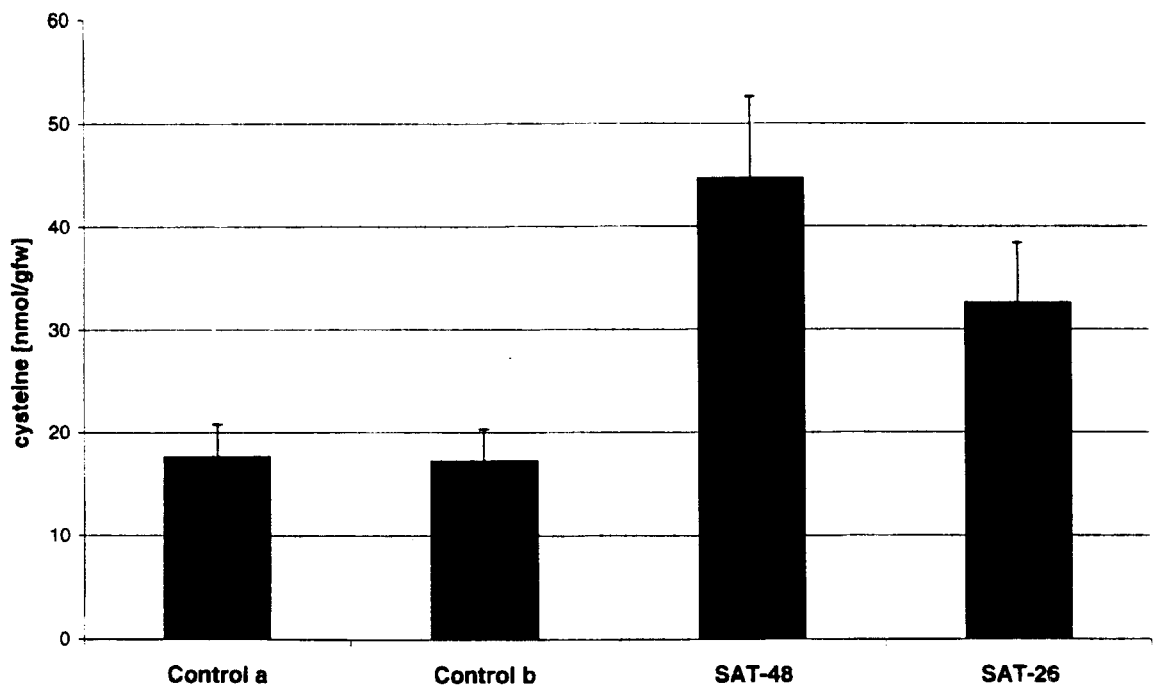
Figure 2B:
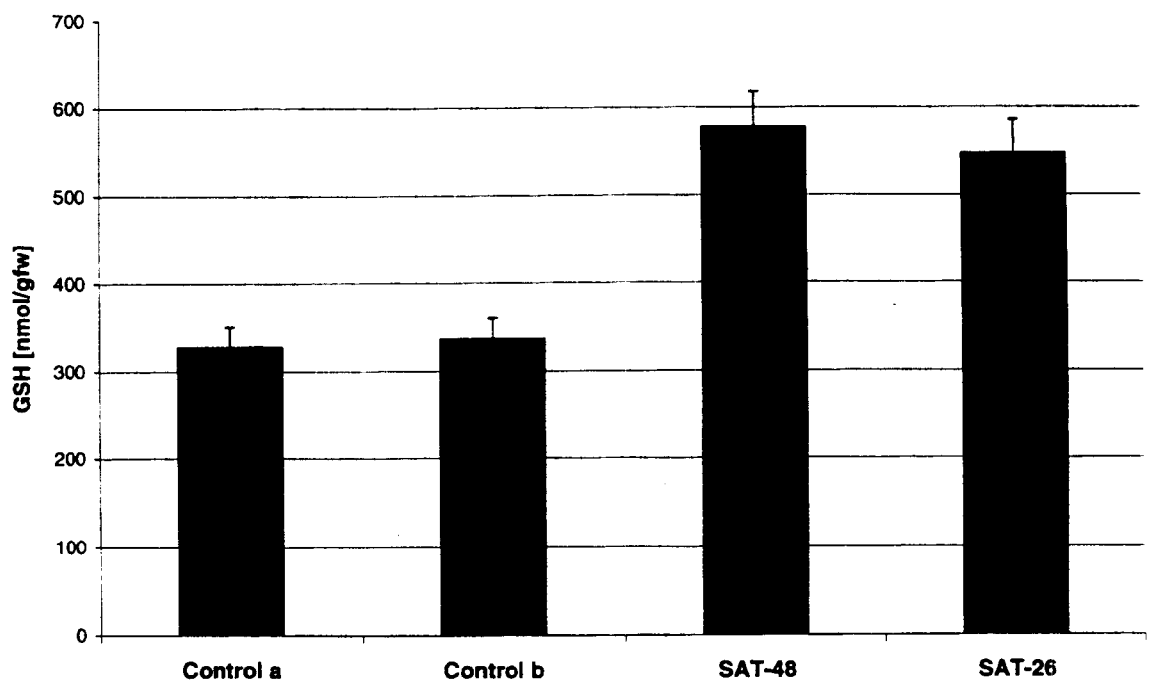

FIG. 2: (a) Endogenous levels of cysteine in leaves of 6-week old transgenic (SAT-48 and SAT-26) and wild type plants (Control a and b). Amounts of cysteine are given in nmol per gfw. Error bars represent standard deviation (<20). N=18; 6 independent plants per transgenic line, 3 independent measurements per plant.

(b) Endogenous levels of glutathione in leaves of 6-week old transgenic (SAT-48 and SAT-26) and wild type plants (Control a and b). Amounts of glutathione are given in nmol per gfw. Error bars represent standard deviation (<10). N=18; 6 independent plants per transgenic line, 3 independent measurements per plant.

Figure 3:
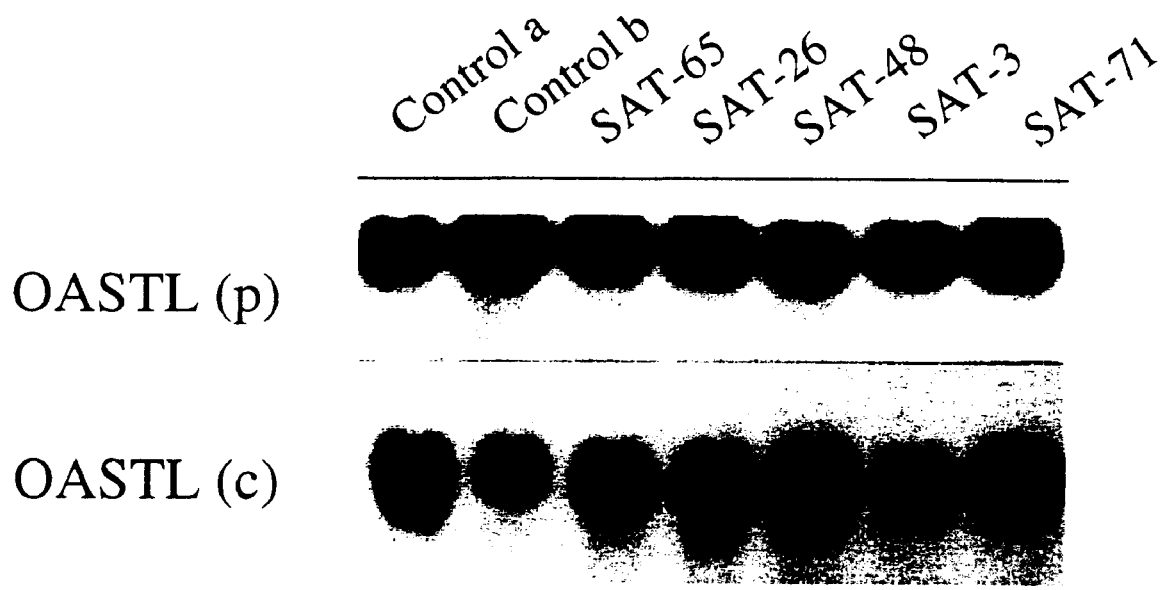

FIG. 3: Northern blot analysis of total RNA extracted from leaves of five independent transgenic (SAT-65, 26, 48, 3 and 71) and two wild type plants (Control a and b). The blot was probed with $^{32}$P-labeled plastidic potato OAS-TL cDNA (p) and also with a cytosolic isoform (c). The lanes contained 15 µg of total RNA each.

Figure 4:
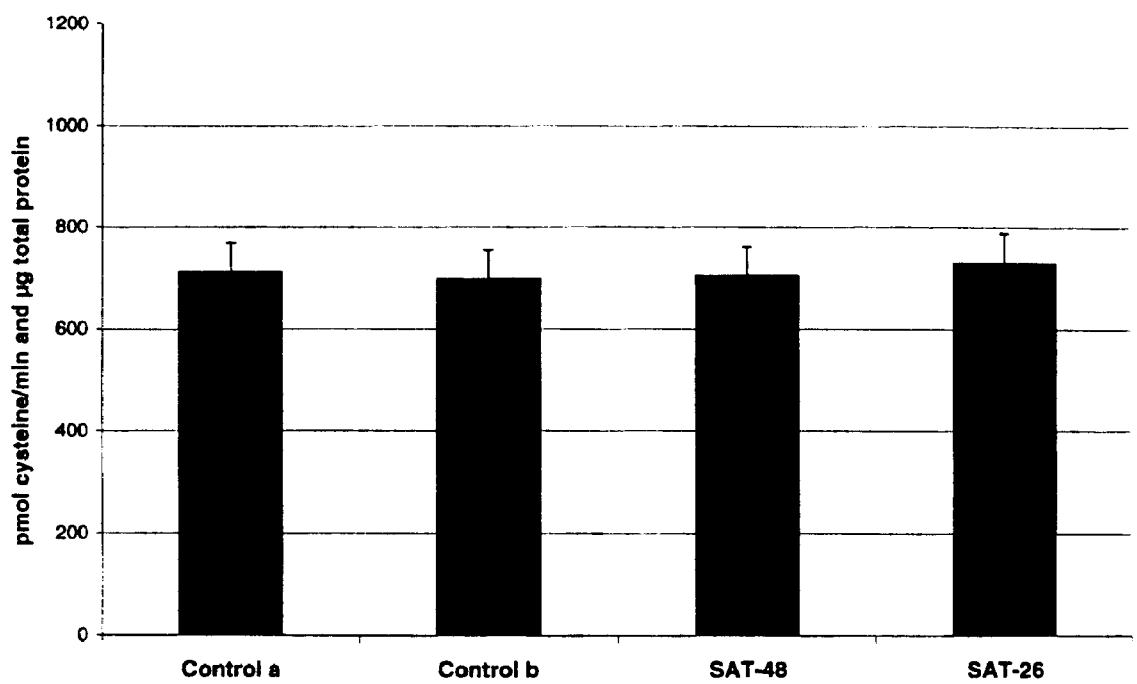

FIG. 4: In vitro OAS-TL activity in leaves of transgenic (SAT-48 and 26) and wild type plants (Control a and b). The specific activity of crude extracts is given in pmol produced cysteine per min and µg total protein. Error bars represent standard deviation (<10%). N=4 independent measurements.

The Examples illustrate the invention:

EXAMPLE 1

Screening for Transgenic Potato Plants Containing the *E. coli* SAT mRNA

To target SAT from *E. coli* to chloroplasts of plants a gene fusion with a Rubisco transit peptide from *Arabidopsis* was constructed. SAT from *E. coli* genomic DNA was amplified by PCR using two synthetic oligonucleotides (EcSAT-N: 5'-GAG AGA CCA TGG CGT GTG AAG AAC TGG AAA (SEQ ID NO: 1), EcSAT-C: 5'-GAG AGA TCT AGA TTA GAT CCC ATC CCC ATA (SEQ ID NO: 2)) Double stranded DNA was digested with Nco I and Xba I and cloned behind the transit peptide. The fused gene product was inserted as Asp 718/Xho I fragment into a with Asp 718/Sal I predigested binary vector (Höfgen and Willmitzer, 1990) under the contol of the 35S-CaMV promoter. The plasmid was introduced into potato via *Agrobacterium tumefaciens* (Solanum tuberosum cv Désirée) as described by Rocha-Sosa et al. (1989). Solanum tuberosum cv Désirée was obtained from Vereinigte Saatzuchten eG (Ebstorf, Germany). Wild type and transgenic plants were kept in tissue culture under a 16-hours-light/8-hours-dark period on Murashige and Skoog medium (Murashige and Skoog, 1962) supplemented with 2% (w/v) sucrose at 22° C. In the greenhouse, plants were grown at 22° C. during the light period (16 hours) and 15° C. during the dark period (8 hours). The plants were cultivated in separate pots and watered continuously.

Figure 1B:
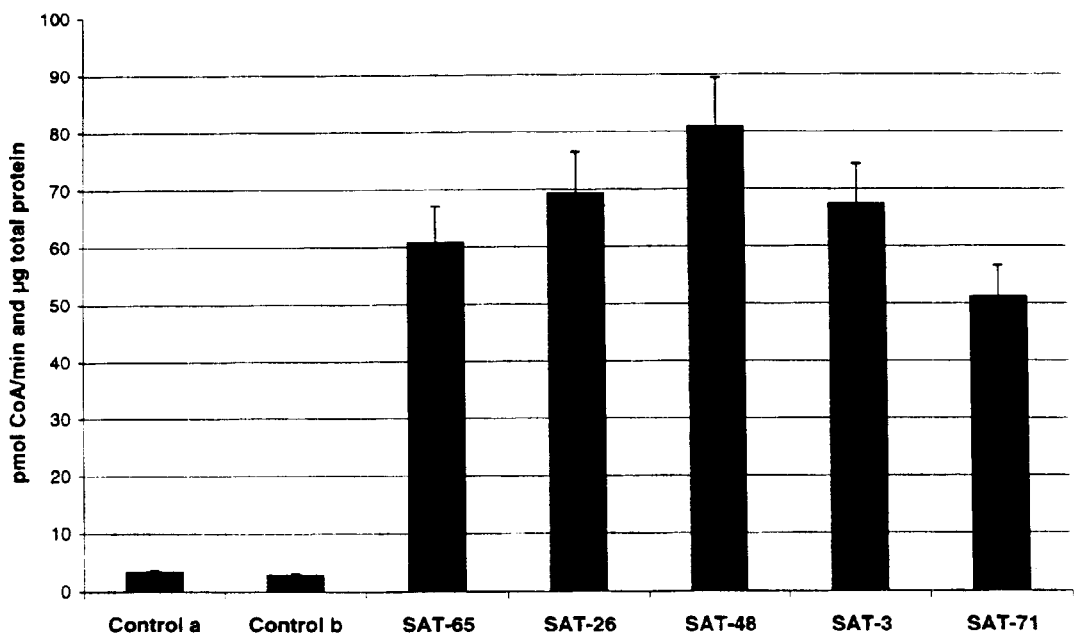

Transgenic potato plants maintained in tissue culture were visually indistinguishable from nontransformed control plants. To screen for plants expressing the *E. coli* SAT mRNA, fifty plants were randomly selected for taking leaf samples. These samples were subjected to RNA gel blot analysis using a radioactively labelled *E. coli* SAT cDNA as a probe. For RNA isolation, plant leaf material was frozen in liquid nitrogen directly after harvest. Total RNA was extracted from the frozen material according to Logemann et al. (1987). After denaturation at 65° C. the total RNA was separated under denaturing conditions by gel electrophoresis (Lehrach, 1977) and then transferred to nylon membranes. Northern hybridisation was performed at an appropriate temperature as described by Amasino (1986). The northern blots were washed three times for 30 min at 55° C. in 0,5×SSC; 0,2% SDS. $^{32}$P-labelling of the fragments was performed with the "Multiprime DNA-labelling-Kit" (Amersham Buchler, Braunschweig, Germany). Five independent transformants accumulating high amounts of the foreign SAT mRNA, were selected for further analysis and transferred into the greenhouse. Repeated Northern analysis revealed, that also under greenhouse conditions the transformants accumulated high amounts of the foreign mRNA (FIG. 1a). The length of the transcript detected in the transgenic potato plants (~1050 basepairs) was in agreement with the length reported for the cysE gene, namely 819 bp (Denk and Böck, 1987) and the used signal sequence of rubisco (~240 bp). For measuring the enzyme activity of SAT an assay was used by following a method of Kredich and Tomkins (1966). This method is based on a disulfide interchange between CoA, liberated from ace tyl-residue during the SAT catalyzed reaction, and 5,5'-dithio-bis-(2-nitro-benzoic acid). The formation of CoA was assayed in 50 mM Tris-HCl (pH 7,6) containing 1 mM 5,5'-dithio-bis-(2-nitro-benzoic acid), 1 mM EDTA, 20 mM L-serine and 100 µM acetyl-CoA. The reaction was started by the addition of 10 µl of crude leaf extract (1,5 µg/µl total protein), the incubation temperature was 25° C. The production of thionitrobenzoic acid was monitored at 412 nm in an spectrophotometer (Ultraspec 2000, Pharmacia Biotech, Uppsala, Sweden) against a blank control containing all materials except L-serine. A calibration curve was established with control solutions containing all materials and different concentrations of CoA (0–200 nmol/ml). The activity assay was repeated independently with different volumes of crude leaf extract, i.e. 20, 40 and 60 µl. The analysis of SAT activity in crude leaf extracts revealed that potato plants expressing the *E. coli* gene convert serine to OAS much more efficiently than do the nbntransformed control plants (FIG. 1b), suggesting that the transformed plants possess increased SAT activity, which is probably due to the foreign *E. coli* serine acetyltransferase. Despite the strong increase in SAT activity in the leaves of transgenic plants, no dramatic change in the phenotype of these plants was visible with only one exception: the transformant 48 showed a reduced apical dominance resulting in a bushy phenotype. Interestingly the transformant 48 had the highest SAT activity from all transgenic plants.

EXAMPLE 2

Expression of the cysE Gene Leads to an Increase in the Endogenous Levels of Cysteine and Glutathione Cysteine biosynthesis in plants takes place via a two step reaction. The formation of cysteine from sulfide and O-acetyl-L-serine is catalyzed by O-acetylserine(thiol)lyase. O-acetyl-L-serine is synthesized by serine acetyltransferase from acetyl-coenzyme A and serine (Brunold and Rennenberg, 1997). To investigate whether the expression of the cysE gene in potato plants influences the endogenous levels of cysteine, the concentration of this sulfur containing amino acid in nontransformed and transformed plants was determined. Thiols were prepared as described by Rüegsegger and Brunold (1992). Seperation and quantification were performed by reverse-phase HPLC after derivatization with monobrnmobimane according to Newton et al. (1981). As a modification, reduction of disulfides was done with bis-2-mercaptoethylsulfone and the labelling reaction with monobromobimane was stopped with 15% HCl.

Frozen leaf material was homogenized to a fine powder and then extracted 20 min in 0,1 N HCl (2 ml/0,2 gfw) at 4° C. After centrifugation of the mixture at 4° C. (20 min, 14.000 g), 120 µl of the supernatent were added to 200 µl of 0,2 M 2-(cyclohexylamino)ethanesulfonic acid (pH 9,3). Reduction of total disulfides was performed by adding 10 µl bis-2-mercaptoethylsulfone in 9 mM Tris-HCl, 5 mM EDTA (pH 8). After the reaction time of 40 min at room temperature, free thiolgroups were labelled with monobromobimane. To this end, 20 μl of 15 mM monobromobimane in acetonitrile were added to the mixture and kept for 15 min in the dark at room temperature. The reaction was stopped by adding 250 μl 15% HCl. After keeping on ice for two hours in the dark, the reaction mixture was again centrifuged at 4° C. (10 min, 14.000 g). For cysteine and glutathione analysis, the supernatent was suitably diluted with 0,1 N HCl. The samples were analysed according to the method of Schupp and Rennenberg (1988) on a reverse phase HPLC column ($C_{18}$, 250×4 mm, 5 μm particle size, Macherey-Nagel, Oensingen, Switzerland). A solvent system consisting of 10% methanol; 0,25% acetic acid, pH 3,9 (NaOH) and 90% methanol; 0,25% acetic acid with a flow rate of 1,5 ml/min was used. Chromatography was followed by fluorescence detection (excitation: 380 nm, emission: 480 nm, SFM 25 fluorescence detector, Kontron, Zürich, Switzerland). Chromatograms were quantified by integration of peak areas. For cysteine analysis the two transformants with the highest SAT-activity were used, i.e. SAT-48 and SAT-26 (see FIG. 2b). To this end, young and green leaves of 5 weeks old plants were harvested and extracted, and the cysteine content was determined via HPLC. Transgenic potato plants expressing the cysE gene from *E. coli* exhibited significantly increased levels of cysteine (FIG. 3a). The levels of the transformant SAT-48 were nearly threefold (45±10 nmol per gram fresh weight of leaf tissue) and of the transformant SAT-26 twofold higher (33±6 nmol/gfw) than those amounts found in nontransformed control plants (17±3 nmol/gfw), indicating that the expression of cysE leads to an increase in the endogenous levels of the amino acid cysteine.

One of the major sinks of cysteine produced by the sulfate-assimilation/reduction cascade is the formation of glutathione, a tripeptide consisting of the aminoacids glutamate, cysteine and glycine. Because the transgenic potato plants expressing the *E. coli* SAT contained more cysteine, it is possible that this could have an effect on the biosynthesis of glutathione, keeping in mind that cysteine is one substrate for glutathione production. To investigate whether this is the case, the levels of glutathione in leaves of the transgenic lines SAT-48 and SAT-26 and of wild type plants were analysed. These measurements revealed that both transformants had significantly elevated glutathione levels, being up to twofold higher (500–600 nmol/gfw) than in wild type plants (300–350 nmol/gfw; FIG. 3b). This suggests that increased levels of cysteine stimulate glutathione biosynthesis.

Taking into account that one molecule glutathione contains one molecule cysteine and that the total molar amounts of glutathione in potato leaves are over 10-fold higher than the molar amounts of the free amino acid cysteine, one can conclude that the synthetic capacity for cysteine in the transgenic potato plants is much stronger increased than only two or threefold as could be thougth by only looking at the levels of free cysteine. An absolute increase of 200–300 nmol glutathione/gfw in the transgenic plants is therefore equivalent with an approximately 10 to 18 fold increased cysteine biosynthetic capacity, when having about 15–20 nmol cysteine/gfw in leaves of wildtyp plants. Add to this the increased levels of free cysteine in the transgenic plants by about two or threefold, the cysteine biosynthesis in the transformants is up to 20 fold upregulated as compared to control plants.

EXAMPLE 3

Increased Endogenous Levels of Cysteine and Glutathione do not Influence the Expression Pattern of OAS-TL Isoforms A metabolically significant regulation of SAT activity by allosteric inhibition of cysteine has been reported for the enzyme from watermelon (Saito, 1995). Bacterial SATs are on transcriptional level feed back inhibited by micromolar concentrations of cysteine. In contrast in a situation of cysteine limitation, the expression of bacterial SATs is stimulated (Kredich, 1987). Additionally, O-acetylserine (thiol)lyase, which is the enzyme directly following after the SAT in the cysteine biosynthesis reaction cascade, is also regulated by cysteine on transcriptional level. The expression of different cDNAs encoding for compartment specific isoforms of O-acetylserine(thiol)lyase from Arabidopsis was observed to be stimulated in plants grown with limited sulfate supply (Hell, 1994; Barroso, 1995; Hesse, 1997). Also in spinach the expression of O-acetylserine(thiol)lyase isoforms is slightly upregulated under sulfur-starved conditions (Takahashi and Saito, 1996). To investigate whether the enhanced levels of cysteine in the transgenic potato plants expressing the cysE gene from *E. coli* influences the expression pattern of the endogenous potato OAS-TL, leaf samples were taken from transgenic and nontransformed plants and subjected to RNA blot analysis; see Example 1. For radioactive labelling of the potato OAS-TL cDNAs (Hesse and Höfgen, 1998), DNA was cut with the appropriate restriction enzymes and seperated on a 1% agarose gel. The DNA fragments were isolated from the gel using the "NucleoSpin Extract" kit from Macherey-Nagel (Düren, Germany). This analysis revealed that although the transgenic plants contained significant more cysteine in their leaves, potato OAS-TL genes (both a cytosolic and a chloroplastidic isoform, Hesse and Högen, 1998) were not altered in their transcription rate compared to the expression in wild type plants (FIG. 3). This suggests that the increased levels of cysteine in the transgenic potato plants have no detectable influence on the expression pattern of the potato OAS-TL on transcriptional level.

EXAMPLE 4

Increased Endogenous Levels of Cysteine do not Influence the Activity of O-acetylserine(thiol)lyase OAS-TL is regulated on activity level by the sulfur state within the cell. The activity of a cytosolic O-acetylserine (thiol)lyase from *Arabidopsis thaliana for* example is activated by sulfur limitation (Barroso, 1995; Hesse, 1997). Increasing of specific activity by sulfur depletion have also been observed in cultured tobacco and *C. reinhardtii* cells and in maize leaves (Bergmann, 1980; Passera and Ghisi, 1982; León, 1988). In contrast high concentrations of sulfur seem to decrease OAS-TL activity. The enzyme from *Datura innoxia* for example is inhibited by higher sulfide concentrations (Kuske, 1994). In *C. reinhardtii* cells OAS-TL activity is inhibited not only by sulfide, but also by OAS and cysteine (León and Vega, 1991). To find out, whether the increased SAT activity and the altered levels of cysteine and glutathione in the transgenic potato plants have an effect on the activity of OAS-TL, an activity-assay for this enzyme was performed with crude leaf extracts. O-acetylserine (thiol)-lyase activity was assayed by measuring the production of L-cysteine. Each assay was started by the addition of 5 μl crude leaf extract (1 μg/μl total protein). Reactions were conducted in 50 mM $K_2HPO_4$/$KH_2PO_4$ (pH 7,5) in the presence of 5 mM DTT, 10 mM O-acetylserine and 2 mM $Na_2S$ (total volume 100 μl) and allowed to proceed for 20 min at 25° C. They were stopped by addition of 50 μl 20% trichloroacetic acid, and then analysed for L-cysteine production by using the Gaitonde reagent (Gaitonde, 1967). The cysteine content was monitored at 560 nm in a spectrophotometer (Ultraspec 2000, Pharmacia Biotech, Uppsala, Sweden) against a blank control containing all materials except O-acetylserine. Experiments were repeated three times. However, these measurements revealed no difference in the OAS-TL activities between the leaf extracts of wild type and transgenic plants (FIG. 4). So one can speculate, that the higher levels of cysteine and glutathione in the transgenic plants not only have no detectable effect on gene expression level but also have no effect on OAS-TL activity.

EXAMPLE 5

Expression for Transgenic Potato Plants Containing E. coli SAT and Plant CγS mRNA Two transgenic lines expressing E. coli SAT (e.g. SAT-48 and SAT-26) were selected for superinfection with a binary plasmid construct containing a CγS cDNA e.g. potato under the control of the 35S- and B33 promoter, respectively. The binary vector is a pBIN19-derivative permitting e.g. hygromycine resistance for plant selection. The plasmids were introduced into the transgenic lines SAT48 and -26, respectively via Agrobacterium tumefaciens as described by Rocha-Sosa, (1989). Selection conditions were chosen as described under Example 1. Superinfected transgenic lines expressing E. coli SAT and CγS were screened on RNA level (Northern Blot), protein level (Western Blot) and enzymatic activity. Northern Blot experiments were performed as described under Example 1. Lines with high CγS expression were selected for protein content and enzymatic activity. 10 µg protein of each leaf extract were tested in Western Blot for increased protein content with respect to wild type and original used transgenic line. Lines with increased protein content were additionally tested for enzymatic activity. 10 µg, 25 µg, 50 µg and 100 µg leaf extract were incubated together with 10 µCi $^{35}$S-Cysteine and 10 mM Succinylhomoserine for 30 min at 30° C. in a total volume of 200 µl of 50 mM Tris/HCl, pH 7.8 and 10 mM DTT. Reactions were stopped by addition of 50 µl 20% TCA. After neutralization and centrifugation 5 µl of each supernatant were analyzed by thin layer chromatography. A mixture of methanol/acetic acid ethylester/$H_2O$=60:30:10) was used as running solvent. Transgenic plants with high activity are further analyzed for GSH, CγS and Met content.

References

Alscher, Physiol Plant 77 (1989), 457–464
Amasino, Anal Biochem 152 (1986), 304–307
Anderson, Sulfur metabolism in plants. In B J Miflin, P J Lea, eds, The Biochemistry
of Plants. Academic Press, New York (1990), 327–381
Barroso, FEBS Lett 363 (1995), 1–5
Bergmann, Z Naturforsch 35c (1980), 952–957
Bogdanova, FEBS Lett 358 (1995), 43–47
Bogdanova, Plant J 11 (1997), 251–262
Breton, J Biol Chem 265 (1990), 18248–18255
Brunold, Planta 155 (1982), 321–327
Brunold, Academic Publishers, The Hague, The Netherlands (1993), 61–76
Brunold, Prog Bot 58 (1997), 164–186
Cook, Arch Biochem Biophys 178 (1977), 293–302
Delhaize, Plant Physiol 89 (1989), 700–706
Denk, J Gen Microbiol 133 (1987), 515–525
Droux, Arch Biochem Biophys 295 (1992), 379–390
Evans, J Bacteriol 173 (1991), 5457–5469
Gaitonde, Biochem J 104 (1967), 627–633
Ghisi, Plant Physiol 92 (1990), 846–849
Ghisi, Photosynthetica 29 (1993), 543–549
Giovanelli, The biochemistry of plants: A comprehensive treatise, amino acids and derivatives. Academic Press, New York 5 (1980), 453–505
Giovanelli, Academic Publishers, The Hague, The Netherlands (1990), 33–48
Hell, FEBS Lett 351 (1994), 257–262
Hesse, W J Cram et al., eds, Sulphur Metabolism in Higher Plants. Backhuys Publishers, Leiden, The Netherlands (1997), 227–230
Hesse, Plant Phys 116 (1998), 1604
Kredich, J Biol Chem 241 (1966), 4955–4965
Kredich, J Biol Chem 244 (1969), 2428–2439
Kredich, Cellular and Molecular Biology. American Society of Microbiology, Washington D.C. (1987), 419–428
Kredich, Academic Publishers, The Hague, The Netherlands (1993), 37–47
Kuske, J Biol Chem 269 (1994), 6223–6232
Kuske, Plant Physiol 112 (1996), 659–667
Lai, Gene 119 (1992), 113–118
Lehrach, Biochem 16 (1977), 4743–4751
León, J Plant Physiol 132 (1988), 618–622
León, Plant Physiol Biochem 29 (1991), 595–599
Logemann, Anal Biochem 163 (1987), 21–26
Lunn, Plant Physiol 94 (1990), 1345–1352
Meister, Annu Rev Biochem 52 (1983), 711–760
Monroe, J Bacteriol 172 (1990), 6919–6929
Murashige, Physiol Plant 15 (1962), 473–479
Murillo, Cell Mol Biol 41 (1995), 425–433
Nakamura, Plant Cell Physiol 28 (1987), 885–891
Nakamura, Plant Cell Physiol 29 (1988), 689–693
Nakamura, Agric Biol Chem 54 (1990), 649–656
Neuenschwander, Plant Physiol 97 (1991, 253–258
Newton, Anal Biochem 114( 1981), 383–387
Ngo, Can J Biochem 52(1974), 435–440
Noctor, Plant Physiol 112 (1996), 1071–1078
Noji, Mol. Gen. Genet. 244(1994), 57–66
Nussbaum, Plant Physiol 88 (1988), 1407–1410
Ostrowski, J Bacteriol 171 (1989),130–140
Passera, J Exp Bot 33 (1982), 432–438
Rauser, Plant Physiol 97 (1991), 128–138
Ravanel, C R Acad Sci Paris 320 (1997), 497–504
Rennenberg, Plant Physiol 73 (1983), 560–565
Rennenberg, SPB Academic Publishers, The Hague (1990), 276
Rennenberg, Prog Bot 55 (1994), 142–156
Rennenberg, Cambridge University Press, Cambridge, UK (1 995), 155–171
Roberts, Plant Mol Biol 30 (1996), 1041–1049
Rocha-Sosa, EMBO J 8 (1989), 23–29
Rolland, Plant Physiol 98 (1992), 927–935
Rolland, Arch Biochem Biophys 300 (1993), 213–222
Rolland, Eur J Biochem 236 (1996), 272–282
Rüegsegger, Plant Physiol 99 (1992), 428–433
Rufeet, Plant Physiol 104 (1994), 597–604
Ruffet, Eur J Biochem 227 (1995), 500–509
Saito , Proc Natl Acad Sci USA 89 (1992), 8078–8082
Saito, FEBS Lett 324 (1993), 247–252
Saito, J Biol Chem 269(1994), 28187–28192
Saito, Plant Physiol 106 (1994), 887–895
Saito, J Biol Chem 270 (1995), 16321–16326
Schmidt, Annu Rev Plant Physiol Plant Mol Biol 43 (1992), 325–349
Schupp, Plant Sci 57 (1988), 113–117
Smith, Biochem Biophys Res Commun 35 (1969), 939–945
Smith, Biochim Biophys Acta 277 (1971), 288–295
Smith, Plant Physiol 50 (1972), 477–479
Smith, Alscher R G, Cumming J R (eds) Wiley-Liss, New York (1990), 201–215
Takahashi, Plant Physiol 112 (1996), 273–280
Vaara, FEMS Microbiol Lett 97 (1992), 249–254
von Arb, Physiol Plant 67 (1986), 81–86
Vuorio, FEBS Lett 292 (1994), 90–94
Youssefian, Plant J 4 (1993), 759–769

What is claimed is:

1. A recombinant DNA molecule comprising
   (a) a nucleic acid molecule encoding a protein having serine acetyl-transferase (SAT) activity, and optionally
   (b) a nucleic acid molecule encoding a protein having cysteine-γ-synthase (CγS) activity;
   wherein said nucleic acid molecule(s) are operably linked to regulatory elements allowing the expression of the nucleic acid molecule(s) in plant cells.

2. The recombinant DNA molecule of claim 1, wherein said protein having SAT activity is a serine acetyltransferase from prokaryotes or archaebacteria.

3. The recombinant DNA molecule according to claim 1 or 2, wherein the protein having CγS-activity is cysteine-γ-synthase from potato, tobacco, tomato, rape seed or Arabidopsis.

4. The recombinant DNA molecule of claim 3, wherein the nucleic acid molecule of (a) and/or (b) is operably linked to a nucleotide sequence encoding a transit peptide capable of directing the protein(s) into a desired cellular compartment.

5. The recombinant DNA molecule of claim 4, wherein said cellular compartment is a plastid.

6. The recombinant DNA molecule of claim 1, wherein said regulatory elements comprise a promoter active in plant cells.

7. The recombinant DNA molecule of claim 6, wherein said promoter is inducible, constitutively expressed and/or is a cell, tissue or organ specific promoter.

8. The recombinant DNA molecule of claim 7, wherein said promoter is tuber-specific, seed-specific, endosperm-specific, embryo-specific, or phloem-specific.

9. A vector comprising at least one recombinant DNA molecule of claim 1.

10. The vector of claim 9 further comprising a selectable marker.

11. A transgenic plant cell comprising stably integrated into its genome at least one recombinant DNA molecule of claim 1 or at least one vector of claim 8 or 9.

12. The transgenic plant cell of claim 11, comprising a nucleic acid molecule as defined in claim 1(b) encoding a protein having cysteine-γ-synthase (CγS) activity.

13. The transgenic plant cell of claim 11, comprising a selectable marker.

14. A transgenic plant or plant tissue comprising plant cells of claim 11.

15. The transgenic plant of claim 14, wherein the level of glutathione, cysteine and/or methionine is increased compared to a wild type plant.

16. Harvestable parts of a plant of claim 14 or 15.

17. Propagation material of a transgenic plant of claim 14 or 15.

18. A method for the production of transgenic plants which display an increased level of glutathione, cysteine and/or methionine which comprises transforming a plant with at least one recombinant DNA molecule of claim 1.

19. The method of claim 18, wherein said increased level of methionine or cysteine results in accelerated maturation processes, altered flowers and/or pathogen resistance.

20. A method of transforming a plant comprising:
    (a) introducing the recombinant DNA molecule according to claim 1 or 2 into the genome of a plant, plant cell or plant tissue.

* * * * *